United States Patent [19]

Hiroki et al.

[11] Patent Number: 4,560,682
[45] Date of Patent: Dec. 24, 1985

[54] ORGANOPHOSPHORIC ACID ESTERS OF BENZOFURANOLS AND PESTICIDAL COMPOSITIONS THEREOF

[75] Inventors: Ohta Hiroki, Kokubunji; Oda Masatsugu, Machida; Kato Jun, Gotenba, all of Japan

[73] Assignee: Mitsubishi Chemical Industries Ltd., Tokyo, Japan

[21] Appl. No.: 682,006

[22] PCT Filed: Apr. 4, 1984

[86] PCT No.: PCT/JP84/00167
§ 371 Date: Dec. 7, 1984
§ 102(e) Date: Dec. 7, 1984

[87] PCT Pub. No.: WO84/03886
PCT Pub. Date: Oct. 11, 1984

[30] Foreign Application Priority Data

Apr. 7, 1983 [JP] Japan ................................. 58-61331
Aug. 30, 1983 [JP] Japan ................................. 58-158297

[51] Int. Cl.$^4$ .................... A01N 57/16; A01N 57/24; C07F 9/14; C07F 9/18
[52] U.S. Cl. .................... 514/100; 549/220; 549/462
[58] Field of Search .................. 549/220; 514/100

[56] References Cited

U.S. PATENT DOCUMENTS 3,590,052  6/1971  Barker ................................. 260/327
4,303,653 12/1981  Chiyomaru et al. ................. 549/220

FOREIGN PATENT DOCUMENTS 0054589  6/1982  Euro. Pat. Appl.
2004930 12/1969  France.

OTHER PUBLICATIONS

Kumiai Chemical, Chemical Abstracts, vol. 98, (1983) 34, 760m.

Primary Examiner—Richard L. Raymond
Attorney, Agent, or Firm—Oblon, Fisher, Spivak, McClelland & Maier

[57] ABSTRACT

The present invention provides a novel organophosphoric acid ester represented by the following formula, a process for its production and a pesticidal composition containing this ester as an active ingredient:

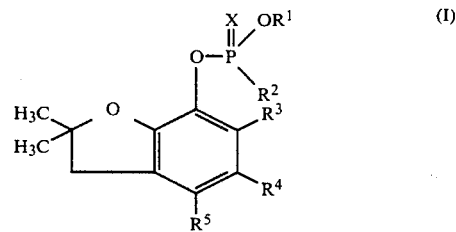

where $R^1$ is an alkyl group, $R^2$ is an alkyl group or a thioalkyl group, each of $R^3$, $R^4$ and $R^5$ is a hydrogen atom, a halogen atom, an alkylthio group, a nitro group, a cyano group, an alkyl group, an alkylsulfinyl group, an alkylsulfonyl group or a trifluoromethyl group, and X is an oxygen atom or a sulfur atom.

8 Claims, No Drawings

ORGANOPHOSPHORIC ACID ESTERS OF BENZOFURANOLS AND PESTICIDAL COMPOSITIONS THEREOF

FIELD OF TECHNOLOGY

The present invention relates to a novel organophosphoric acid ester, a process for its production and a pesticidal composition containing the organophosphoric acid ester.

BACKGROUND OF TECHNOLOGY

Various organic phosphates having pesticidal activities are known. For instance, U.S. Pat. No. 3,839,511 discloses O-ethyl-S-n-propyl-O-(substituted-phenyl)-phosphorothiolates represented by the following formula and their pesticidal activities:

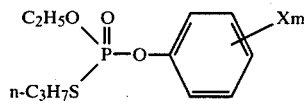

where X is halogen, lower alkyl, nitro, cyano, lower alkylmercapto, lower alkylsulfinyl or lower alkoxycarbonyl, and m is 1 to 3.

However, a phosphate or thiophosphate of benzofuranol has not been known.

On the other hand, in recent years, it has become difficult to control pests by conventional pesticides because the pests have acquired resistance through the extensive use of the pesticides for many years. Under these circumstances, it is desired to develop a new pesticide having a high pesticidal activity and a low phytotoxicity.

SUMMARY OF THE INVENTION

The present invention provides a novel organophosphoric acid ester represented by the following general formula I, a process for its production and a pesticidal composition containing it as an active ingredient:

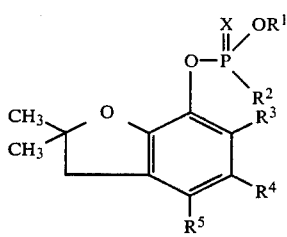

where $R^1$ is an alkyl group, $R^2$ is an alkyl group or a thioalkyl group, each of $R^3$, $R^4$ and $R^5$ is a hydrogen atom, a halogen atom, an alkylthio group, a nitro group, a cyano group, an alkyl group, an alkylsulfinyl group, an alkylsulfonyl group or a trifluoromethyl group, and X is an oxygen atom or a sulfur atom.

In the general formula I, $R^1$ is preferably a $C_1$–$C_4$ alkyl group, more preferably an ethyl group. When X is an oxygen atom, $R^2$ is preferably a $C_1$–$C_4$ alkylthio group, more preferably a propylthio group. When X is a sulfur atom, $R^2$ is preferably a $C_1$–$C_4$ alkyl group or a $C_1$–$C_4$ alkylthio group, more preferably a $C_1$–$C_3$ alkyl group. $R^3$, $R^4$ and $R^5$ may be the same or different and represent a hydrogen atom; a halogen atom, preferably a chlorine atom; a $C_1$–$C_3$ alkylthio group, preferably a methylthio group; a nitro group; a cyano group; a $C_1$–$C_3$ alkyl group, preferably a methyl group; a $C_1$–$C_3$ alkylsulfinyl group, preferably a methylsulfinyl group; a $C_1$–$C_3$ alkylsulfonyl group, preferably a methylsulfonyl group; or a trifluoromethyl group. It is particularly preferred that at least one of $R^3$, $R^4$ and $R^5$, particularly at least one of $R^4$ and $R^5$ is a nitro group, a halogen atom, an alkylthio group or a trifluoromethyl group.

The compounds of the present invention have pesticidal activities. As preferred compounds from the view point of the pesticidal activities, the compounds listed in Table 1 may be mentioned. As particularly preferred compounds, there may be mentioned, for instance, O-ethyl-S-n-propyl-O-(2,3-dihydro-2,2-dimethyl-4-chloro-7-benzofuranyl)-thiophosphate, O-ethyl-S-n-propyl-O-(2,3-dihydro-2,2-dimethyl-5-chloro-7-benzofuranyl)thiophosphate, O-ethyl-S-n-propyl-O-(2,3-dihydro-2,2-dimethyl-4,5-dichloro-7-benzofuranyl)thiophosphate, O-ethyl-S-n-propyl-O-(2,3-dihydro-2,2-dimethyl-4-methylthio-7-benzofuranyl)thiophosphate, O-ethyl-S-n-propyl-O-(2,3-dihydro-2,2-dimethyl-5-methylthio-7-benzofuranyl)thiophosphate, O-ethyl-S-n-propyl-O-(2,3-dihydro-2,2-dimethyl-4-trifluoromethyl-7-benzofuranyl)thiophosphate, O-ethyl-S-n-propyl-O-(2,3-dihydro-2,2-dimethyl-4,5,6-trichloro-7-benzofuranyl)thiophosphate, O-ethyl-S-n-propyl-O-(2,3-dihydro-2,2-dimethyl-5-chloro-4-methylthio-7-benzofuranyl)thiophosphate, and O-ethyl-O-(2,3-dihydro-2,2-dimethyl-4-methylthio-7-benzofuranyl)ethylthionophosphonate.

The organophosphoric acid ester represented by the general formula I may be obtained by reacting a phosphoric acid ester halide represented by the formula II:

where $R^1$, $R^2$ and X are as defined above, and Hal is a halogen atom, with a phenol represented by the formula III:

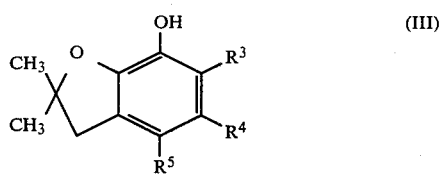

where $R^3$, $R^4$ and $R^5$ are as defined above, optionally in the presence of an acid-binding agent and in the presence of an inert solvent. Or, it may be obtained by reacting the compound of the formula II with a salt of the phenol represented by the formula III in the presence of a solvent.

The reaction of the phosphoric acid ester halide of the formula II with the phenol of the formula III may be conducted in a solvent inert to the reaction, e.g. a ketone such as acetone or methyl ethyl ketone; an aromatic hydrocarbon such as benzene or toluene; or a polar solvent such as tetrahydrofuran, acetonitrile or dimethylformamide.

As the acid-binding agent, there may be employed, an alkali metal carbonate such as sodium carbonate, potassium carbonate or sodium hydrogen carbonate; an alkali metal hydroxide such as sodium hydroxide; an alkali metal hydride such as sodium hydride; or a tertiary amine such as pyridine.

Instead of using the acid-binding agent and the phenol, an alkali metal salt of the phenol of the formula III may be reacted with the phosphoric acid ester halide represented by the formula II.

This reaction is usually conducted by using equimolar amounts of the starting material III or its salt and the phosphoric acid ester halide represented by the formula II. In some cases, it is advantageous to use either one of the reactants in an excess amount. Preferably, the phosphoric acid ester halide represented by the formula II is used in an amount of from 0.9 to 1.1 mols relative to 1 mol of the phenol represented by the formula III.

The reaction temperature is selected within a range of from 0° to 100° C., preferably from 20° to 70° C.

Certain compounds of the present invention may be prepared also by the following method.

Namely, compounds of the present invention represented by the general formula I where $R^2$ is a $C_1$–$C_3$ alkylthio group can be obtained by reacting a phosphate represented by the formula IV.

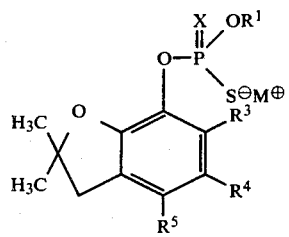
(IV)

where X, $R^1$, $R^3$, $R^4$ and $R^5$ are as defined above, and M is an alkali metal or an ammonium group, with an alkyl halide represented by the formula $R^{2'}$—Hal where $R^{2'}$ is a $C_1$–$C_3$ alkyl group, and Hal is a halogen atom. As the alkali metal used here, there may be mentioned, for instance, lithium, sodium or potassium.

Further, the compounds of the present invention may be produced by another method described below.

Namely, compounds of the general formula I where $R^2$ is a $C_1$–$C_3$ alkylthio group, can be obtained by reacting a phosphoric acid ester halide represented by the formula V:

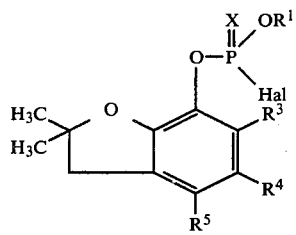
(V)

where X, $R^1$, $R^3$, $R^4$ and $R^5$ are as defined above, and Hal is a halogen atom, with an alkyl mercaptan represented by the formula $R^{2'}SH$ where $R^{2'}$ is as defined above.

The phosphoric acid ester halide represented by the formula II is a known compound, and may be prepared by a known method. (See J. Org. Chem., 30, 3217(1965); Japanese Examined Patent Publication No. 11716/1981; and J. Agr. Food. Chem., 17, 863(1969)).

The phonol of the formula III as another starting material may also be prepared by a known method or in accordance with a known method. For instance, 2,3-dihydro-2,2-dimethyl-7-benzofuranol is disclosed in Japanese Examined Patent Publication No. 9546/1968 and its methyl-substituted compound is disclosed in British Pat. No. 1,179,250. Further, its halogen-substituted compounds can be obtained by reacting 2,3-dihydro-2,2-dimethyl-7-benzofuranol with a halogenating agent in accordance with e.g. U.S. Pat. No. 3,474,170. As the halogenating agent, there may be mentioned, for instance, chlorine, phosphorus pentachloride, sodium perchlorate, sulfuryl chloride, N-chlorosuccimide, bromine, phosphorus pentabromide or N-bromo succimide. Its nitro-substituted compound may be obtained either by reacting 2-3-dihydro-2,2-dimethyl-7-benzofuranol with a nitrating agent such as nitric acid, fuming nitric acid or a mixed acid in a solvent such as paraffin, ether, chloroform or water, or by reacting the halogen-substituted compound with a nitrate such as sodium nitrate or silver nitrate.

The cyano-substituted derivative of 2,3-dihydro-2,2-dimethyl-7-benzofuranol may be obtained by reacting the halogen-substituted compound with copper cyanide or sodium cyanide in a polar solvent such as dimethylformamide.

It is further possible to obtain a 2,3-dihydro-2,2-dimethyl-4-substituted-7-benzofuranol by using a 2-nitro-5-substituted phenol as the starting material and by subjecting it to methallyl etherification, thermal rearrangement, reduction and hydrolysis of the diazonium salt, successively in accordance with the method disclosed in Japanese Examined Patent Publication No. 9546/1968. This method is particularly suitable for a case where the substituent is a halogen atom, an alkyl group, an alkylthio group or a trifluoromethyl group. Further, by using a 2-nitro-4-substituted phenol, a 5-substituted derivative may be obtained in the same manner.

The alkylsulfinyl-substituted derivative and the alkylsulfonyl-substituted derivative may be obtained by subjecting the corresponding alkylthio-substituted derivative to a known oxidation method, for instance, by reacting it with an oxidizing agent such as hydrogen peroxide or m-chloro perbenzoic acid.

The compounds of the general formula I obtained by the present invention, have remarkable insecticidal and acaricidal activities, and particularly effective when contacted to or took in by pests. They exhibit particularly remarkable pesticidal activities against such pests as Lepidoptera such as tobacco cutworm (*Prodenia litura fabricius*) or diamondback moth (*Plutella maculipennis curtis*); Hemiptera such as green rice leafhopper (*Nephotettix cincticeps uhler*), brown plant hoppers (*Nilaparvata lugens stal*) or green peach aphids (*Myzus percicae sulzer*); Coleoptera such as adzuki bean weevil (*Callosobruchus chinensis linne*); Diptera such as housefly; Acarina such as two spotted spide mite (*Tetranychus truncatus ehara*).

When the compounds of the formula I are to be used as pesticides, they may be used by themselves. However, they are usually formulated into an emulsion, a dust, a wettable powder or an emulsifiable concentrate, with use of adjuvants as in the case of conventional agricultural chemicals, and then used as such or after being diluted. As the adjuvants, those commonly used in the pesticidal formulations may be employed. For instance, there may be mentioned a solid carrier such as talc, kaolin, diatomaceous earth, clay or starch; a solvent such as water, a hydrocarbon such as cyclohexane, benzene, xylene or toluene, a halogenated hydrocarbon such as chlorobenzene, an ether, dimethylformamide, a ketone, an alcohol or acetonitrile; or other known surfactants such as an emulsifying agent or a dispersing agent.

Further, if desired, they may be used in combination with other insecticides, acaricides, bactericides, insect growth-regulating agents or plant growth-regulating agents.

The concentration of the active ingredient in the formulated pesticidal compositions is not limited to a particular range. However, the concentration is usually from 0.5 to 20% by weight preferably from 1 to 10% by weight, in the case of a dust, from 1 to 90% by weight, preferably from 10 to 40% by weight, in the case of a wettable powder, from 1 to 90% by weight, preferably from 10 to 40% by weight in the case of an emulsion, or from 0.5 to 40% by weight, preferably from 1 to 20% by weight, in the case of a granule.

When the compounds of the formula I are to be used as pesticides, they are usually used in a concentration within a range of from 10 to 1,000 ppm, preferably from 50 to 500 ppm, as the active ingredient.

Now, the present invention will be described in further detail with reference to Examples for the preparation, formulation and testing of the compounds of the present invention. However, the present invention is by no means restricted to such specific Examples.

EXAMPLE 1

O-Ethyl-S-n-propyl-O-(2,3-dihydro-2,2-dimethyl-7-benzofuranyl)thiophosphate

To a solution of 2,3-dihydro-2,2-dimethyl-7-benzofuranol (16.4 g, 0.1 mol) in 200 ml of acetone, anhydrous potassium carbonate (13.8 g, 0.1 mol) was added, and then O-ethyl-S-n-propylthiophosphoryl chloride (20.3 g, 0.1 mol) was gradually added. The reaction mixture was heated and refluxed for 2 hours under stirring.

Insoluble solid substances were removed by filtration. The filtrate was concentrated and the residue thereby obtained was purified by silica gel column chromatography, whereby the compound (No. 1) identified in Table 1 was obtained.

EXAMPLE 2

O-Ethyl-S-n-propyl-O-(2,3-dihydro-2,2-dimethyl-7-benzofuranyl)dithiophosphate

In the same manner as in Example 1, 2,3-dihydro-2,2-dimethyl-7-benzofuranol and O-ethyl-S-n-propyldithiophosphoryl chloride were reacted to obtain the compound (No. 2) identified in Table 1.

EXAMPLE 3

O-Ethyl-S-n-propyl-O-(2,3-dihydro-2,2-dimethyl-4-nitro-7-benzofuranyl)thiophosphate To a solution of 2,3-dihydro-2,2-dimethyl-7-benzofuranol (16.4 g, 0.1 mol) in 150 ml of ether, 70% nitric acid (9.0 g, 0.1 mol) was slowly dropwise added at room temperature. The reaction solution was stirred for further 20 minutes, then washed with water, dried over anhydrous sodium sulfate and concentrated. The solid substance thereby obtained, was repeatedly recrystallized from hexane-ethyl acetate, whereby 6.2 g of 2,3-dihydro-2,2-dimethyl-4-nitro-7-benzofuranol and 6.0 g of 2,3-dihydro-2,2-dimethyl-6-nitro-7-benzofuranol as its 6-nitro isomer, were obtained. The melting points of these products were 164°–165° C. and 125°–126° C., respectively. Further, the structures of these intermediate phenols were confirmed by $^1$H-NMR spectra. 2,3-Dihydro-2,2-dimethyl-4-nitro-7-benzofuranol thus obtained, was reacted with O-ethyl-S-n-propylthiophosphoryl chloride in the same manner as in Example 1, whereby the compound (No. 6) identified in Table 1 was obtained.

EXAMPLE 4

O-Ethyl-S-n-propyl-O-(2,3-dihydro-2,2-dimethyl-5-nitro-7-benzofuranyl)thiophosphate 2,3-Dihydro-2,2-dimethyl-7-benzofuranol (16.4 g, 0.1 mol) was dissolved in 100 ml of an aqueous solution of sodium hydroxide (6.0 g, 0.15 mol), and 12.8 g of acetic anhydride was dumped into the solution and thoroughly mixed, whereby a white solid substance was precipitated. This substance was collected by filtration and dried, whereby 19.5 g of 7-acetoxy-2,3-dihydro-2,2-dimethylbenzofuran was obtained. The melting point of this product was 48.5°–49.5° C. This phenol acetate was dissolved in 400 ml of chloroform, and 60 ml of 70% nitric acid was dropwise added at −5° C. Then, the stirring was continued at 10° C. for one hour. The reaction solution was washed with water, then dried over anhydrous sodium sulfate and concentrated. The solid substance thereby obtained was recrystallized from benzene-cyclohexane, whereby 19.6 g of 7-acetoxy-2,3-dihydro-2,2-dimethyl-5-nitrobenzofuran was obtained. The melting point of this product was 141°–142° C. The structure was confirmed by $^1$H-NMR spectrum and IR spectrum. Then, the product was added to a solution containing 35 g of sodium hydroxide in 200 ml of water and 50 ml of methanol, and heated at 40° C. for 15 minutes to complete hydrolysis. The reaction solution was neutralized by concentrated hydrochloric acid, and then extracted with ether. The extracted solution was washed with water, then dried over anhydrous sodium sulfate and concentrated, whereby 13.0 g of substantially pure 2,3-dihydro-2,2-dimethyl-5-nitro-7-benzofuranol was obtained. The melting point of this product was 97°–97.5° C. The phenol thus obtained, was reacted with O-ethyl-S-n-propyl-thiophosphoryl chloride in the same manner as in Example 1, whereby the compound (No. 4) identified in Table 1 was obtained as oily substance.

EXAMPLE 5

O-Ethyl-S-n-propyl-O-(5-chloro-2,3-dihydro-2,2-dimethyl-7-benzofuranyl)dithiophosphate To a solution of 2,3-dihydro-2,2-dimethyl-7-benzofuranyl methylcarbamate (33.2 g, 0.15 mol) in 150 ml of chloroform and 300 ml of carbon tetrachloride, chlorine (10.7 g, 0.15 mol) was gradually fed at a temperature of from 10° to 15° C. under stirring. The precipitated crystals were collected by filtration and washed with hexane, whereby 34.1 g of 5-chloro-2,3-dihydro-2,2-dimethyl-7-benzofuranyl methylcarbamate was obtained. The melting of this product was 167°–169° C. The structure was confirmed by $^1$H-NMR spectrum. Then, the product was added to 100 ml of a 10% aqueous sodium hydroxide-methanol solution and heated at 80° C. for 3 hours. The reaction solution was neutralized with hydrochloric acid and extracted with ether. The ether layer was washed with water, dried over anhydrous sodium sulfate and concentrated, whereby 23.0 g of 5-chloro-2,3-dihydro-2,2-dimethyl-7-benzofuranol was obtained. The melting point of this product was 65.5°–66.5° C. The phenol thus obtained, was reacted with O-ethyl-S-n-propyldithiophosphoryl chloride in the same manner as in Example 1, whereby the compound (No. 18) identified in Table 1 was obtained.

EXAMPLE 6

O-Ethyl-O-(2,3-dihydro-2,2-dimethyl-7-benzofuranyl)ethylthionophosphonate

To a solution of 2,3-dihydro-2,2-dimethyl-7-benzofuranol (16.4 g, 0.1 mol) in 200 ml of acetone, anhydrous potassium carbonate (13.8 g, 0.1 mol) was added and then O-ethyl-ethylthionophosphonic acid chloride (18.1 g, 0.105 mol) was gradually added. The reaction mixture was heated and refluxed for 3 hours under stirring. Insoluble solid substances were removed by filtration. The filtrate was concentrated, and the residue thereby obtained was purified by silica gel column chromatography, whereby the compound (No. 44) identified in Table 1 was obtained.

EXAMPLE 7

O-Ethyl-O-(2,3-dihydro-2,2-dimethyl-5-methylthio-7-benzofuranyl)-ethylthionophosphonate To a mixture of 2,3-dihydro-2,2-dimethyl-7-benzofuranol (16.4 g), 20 ml of 70% perchloric acid and 16 ml of phosphorus oxychloride, dimethyl sulfoxide (7.8 g, 0.1 mol) was gradually added at a temperature of not higher than 5° C. The reaction solution was stirred at room temperature for further one hour, then poured into ice water and extracted with ethyl acetate. The ethyl acetate layer was washed with water, concentrated and then heated and refluxed, together with 200 ml of pyridine, for 4 hours. Pyridine was concentrated under reduced pressure, and the residue was washed with ether. The ether layer was washed with 1N hydrocloric acid and water successibly, then dried over anhydrous sodium sulfate and concentrated. The solid substance thereby obtained was recrystallized from ether-hexane, whereby 9.7 g of 2,3-dihydro-2,2-dimethyl-5-methylthio-7-benzofuranol was obtained. The melting of this product was 57°–59° C. The structure was confirmed by $^1$H-NMR spectrum and IR spectrum. Then, this phenol derivative was reacted with O-ethyl-ethylthionophosphonic acid chloride in the same manner as in Example 1, whereby the compound (No. 49) identified in Table 1 was obtained.

EXAMPLE 8

O-Ethyl-O-(2,3-dihydro-2,2-dimethyl-4-nitro-5-chloro-7-benzofuranyl)-ethylthionophosphonate To a solution of 2,3-dihydro-2,2-dimethyl-5-chloro-7-benzofuranol (19.8 g, 0.1 mol) in 130 ml of chloroform, 60% nitric acid (10.5 g, 0.1 mol) was slowly dropwise added under cooling with ice. The reaction solution was returned to room temperature and stirred for further 20 minutes. Then, the reaction solution was washed with water, dried over anhydrous sodium sulfate and then concentrated. The residue thereby obtained, was purified by silica gel chromatography, whereby 12.3 g of 2,3-dihydro-2,2-dimethyl-4-nitro-5-chloro-benzofuranol was obtained. The structure of this product was confirmed by $^1$H NMR spectrum. The phonol derivative thus obtained, was reacted with O-ethyl-ethylthionophosphonic acid chloride in the same manner as in Example 1, whereby the compound (No. 63) identified in Table 1 was obtained.

EXAMPLE 9

O-Ethyl-O-(2,3-dihydro-2,2-dimethyl-5-cyano-7-benzofuranyl)-ethylthionophosphonate A mixture of 2,3-dihydro-2,2-dimethyl-5-bromo-benzofuranol (17.8 g, 73.3 mmol), copper cyanide (7.6 g, 84.9 mmol) and 15 ml of DMF, was heated and refluxed for 3 hours under stirring, and then added to 55 ml of an aqueous sodium cyanide solution (NaCN: 16 g, 326 mmol). The organic layer thereby formed, was extracted with ethyl acetate, and the extracted solution was washed with a saturated sodium chloride aqueous solution and then dried over anhydrous sodium sulfate. After concentration, the residue was purified by silica gel column chromatography, whereby 12.5 g (66.1 mmol, yield: 85%) of 2,3-dihydro-2,2-dimethyl-5-cyano-5-benzofuranol was obtained. The structure of this product was confirmed by $^1$H NMR spectrum and IR spectrum. The melting point of the product was 149.5°–150.5° C. The intermediate phenol thus obtained, was reacted with O-ethyl-ethylthionophosphonic acid chloride in the same manner as in Example 1, whereby the compounds (No. 51) identified in Table 1 was obtained.

EXAMPLE 10

O-Ethyl-S-n-propyl-O-(2,3-dihydro-2,2-dimethyl-4-trifluoromethyl-7-benzofuranyl)thiophosphate 2,3-Dihydro-2,2-dimethyl-4-trifluoromethyl-7-benzofuranol (23.2 g, 0.1 mol) was gradually added to a suspension of 4.8 g of 50% sodium hydride in 300 ml of dried dimethylformamide under cooling. Then, O-ethyl-S-n-propylthiophosphoryl chloride (20.3 g, 0.1 mol) was gradually added under cooling with ice. The reaction mixture was stirred for 2 hour at room temperature, and then poured into ice water. The oily substance was extracted with ether. The organic layer was dried over anhydrous sodium sulfate, concentrated and then purified by silica gel column chromatography, whereby the compound (No. 36) identified in Table 1 was obtained.

The representative compounds of the present invention prepared in a similar manner, are shown in Table 1.

TABLE 1

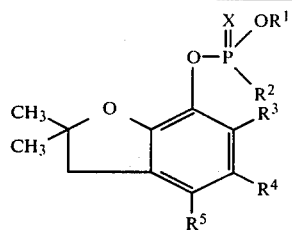

| Compound No. | $R^1$ | $R^2$ | $R^3$ | $R^4$ | $R^5$ | X | Physical Property |
|---|---|---|---|---|---|---|---|
| 1 | $C_2H_5$ | $S-C_3H_7$ | H | H | H | O | $N_D^{25}$ 1.5211 |
| 2 | $C_2H_5$ | $S-C_3H_7$ | H | H | H | S | 1.5492 |
| 3 | $C_2H_5$ | $S-C_3H_7$ | $NO_2$ | H | H | O | 1.5378 |
| 4 | $C_2H_5$ | $S-C_3H_7$ | H | $NO_2$ | H | O | 1.5360 |
| 5 | $C_2H_5$ | $S-C_3H_7$ | H | $NO_2$ | H | S | 1.5760 |
| 6 | $C_2H_5$ | $S-C_3H_7$ | H | H | $NO_2$ | O | 1.5340 |
| 7 | $C_2H_5$ | $S-C_3H_7$ | H | H | $NO_2$ | S | 1.5630 |
| 8 | $C_2H_5$ | $S-C_3H_7$ | H | CN | H | O | 1.5273 |
| 9 | $C_2H_5$ | $S-C_3H_7$ | H | H | CN | O | 1.5390 |
| 10 | $C_2H_5$ | $S-C_3H_7$ | H | H | CN | S | 1.5555 |
| 11 | $C_2H_5$ | $S-C_3H_7$ | H | $SCH_3$ | H | O | 1.5460 |
| 12 | $C_2H_5$ | $S-C_3H_7$ | H | $SCH_3$ | H | S | 1.5440 |
| 13 | $C_2H_5$ | $S-C_3H_7$ | H | H | $SCH_3$ | O | 1.5459 |
| 14 | $C_2H_5$ | $S-C_3H_7$ | H | H | $S-i-C_3H_7$ | O | 1.5370 |
| 15 | $C_2H_5$ | $S-C_3H_7$ | H | $SOCH_3$ | H | O | 1.5375 |
| 16 | $C_2H_5$ | $S-C_3H_7$ | H | $SO_2CH_3$ | H | O | m.p. 100–100.5° C. |
| 17 | $C_2H_5$ | $S-C_3H_7$ | H | Cl | H | O | $N_D^{25}$ 1.5241 |
| 18 | $C_2H_5$ | $S-C_3H_7$ | H | Cl | H | S | 1.5531 |
| 19 | $C_2H_5$ | $S-C_3H_7$ | H | H | Cl | O | 1.5268 |
| 20 | $C_2H_5$ | $S-C_3H_7$ | H | H | Cl | S | 1.5533 |
| 21 | $C_2H_5$ | $S-C_3H_7$ | H | H | F | O | 1.5070 |
| 22 | $C_2H_5$ | $S-C_3H_7$ | H | H | F | S | 1.5321 |
| 23 | $C_2H_5$ | $S-C_3H_7$ | H | Br | H | O | 1.5335 |
| 24 | $C_2H_5$ | $S-C_3H_7$ | H | Br | H | S | $N_D^{25}$ 1.5584 |
| 25 | $C_2H_5$ | $S-C_3H_7$ | H | H | Br | O | 1.5375 |
| 26 | $C_2H_5$ | $S-C_3H_7$ | H | H | Br | S | 1.5660 |
| 27 | $C_2H_5$ | $S-C_3H_7$ | Cl | H | Cl | O | 1.5335 |
| 28 | $C_2H_5$ | $S-C_3H_7$ | Cl | H | Cl | S | 1.5600 |
| 29 | $C_2H_5$ | $S-C_3H_7$ | H | Cl | Cl | O | 1.5339 |
| 30 | $C_2H_5$ | $S-C_3H_7$ | H | Cl | Br | O | 1.5459 |
| 31 | $C_2H_5$ | $S-C_3H_7$ | H | Br | Cl | O | 1.5434 |
| 32 | $C_2H_5$ | $S-C_3H_7$ | H | Br | Br | O | 1.5550 |
| 33 | $C_2H_5$ | $S-C_3H_7$ | Cl | Cl | Cl | O | 1.5458 |
| 34 | $C_2H_5$ | $S-C_3H_7$ | Cl | Br | Cl | O | 1.5548 |
| 35 | $C_2H_5$ | $S-C_3H_7$ | H | $CF_3$ | H | O | 1.4850 |
| 36 | $C_2H_5$ | $S-C_3H_7$ | H | H | $CF_3$ | O | 1.4890 |
| 37 | $C_2H_5$ | $S-C_3H_7$ | H | $CH_3$ | $NO_2$ | O | 1.5378 |
| 38 | $C_2H_5$ | $S-C_3H_7$ | H | $CH_3$ | $S-CH_3$ | O | 1.5330 |
| 39 | $C_2H_5$ | $S-C_3H_7$ | H | $CH_3$ | $S-CH_3$ | S | 1.5630 |
| 40 | $C_2H_5$ | $S-C_3H_7$ | H | Cl | $NO_2$ | O | 1.5408 |
| 41 | $C_2H_5$ | $S-C_3H_7$ | H | Cl | $S-CH_3$ | O | 1.5467 |
| 42 | $C_2H_5$ | $S-C_3H_7$ | H | Cl | $S-CH_3$ | S | 1.5568 |
| 43 | $C_2H_5$ | $S-C_3H_7$ | H | $S-CH_3$ | Cl | O | 1.5575 |
| 44 | $C_2H_5$ | $C_2H_5$ | H | H | H | S | 1.5282 |
| 45 | $C_2H_5$ | $C_2H_5$ | H | $NO_2$ | H | S | m.p. 58–59° C. |
| 46 | $C_3H_7$ | $CH_3$ | H | H | $NO_2$ | S | $N_D^{25}$ 1.5412 |
| 47 | $C_2H_5$ | $C_2H_5$ | H | H | $NO_2$ | S | 1.5518 |
| 48 | $C_3H_7$ | $C_2H_5$ | H | H | $NO_2$ | S | 1.5422 |
| 49 | $C_2H_5$ | $C_2H_5$ | H | $S-CH_3$ | H | S | 1.5700 |
| 50 | $C_2H_5$ | $C_2H_5$ | H | H | $S-CH_3$ | S | 1.5583 |
| 51 | $C_2H_5$ | $C_2H_5$ | H | CN | H | S | 1.5404 |
| 52 | $C_2H_5$ | $C_2H_5$ | H | H | CN | S | 1.5391 |
| 53 | $C_2H_5$ | $C_2H_5$ | H | Cl | H | S | 1.5348 |
| 54 | $C_2H_5$ | $C_2H_5$ | H | H | Cl | S | 1.5342 |
| 55 | $C_2H_5$ | $C_2H_5$ | H | Br | H | S | 1.5476 |
| 56 | $C_2H_5$ | $C_2H_5$ | H | H | Br | S | 1.5470 |
| 57 | $C_2H_5$ | $C_2H_5$ | H | H | F | S | 1.5177 |
| 58 | $C_2H_5$ | $C_2H_5$ | Cl | H | Cl | S | 1.5412 |
| 59 | $C_2H_5$ | $C_2H_5$ | H | Cl | Cl | S | 1.5450 |
| 60 | $C_2H_5$ | $C_2H_5$ | H | $CH_3$ | $S-CH_3$ | S | 1.5472 |
| 61 | $C_2H_5$ | $C_2H_5$ | H | $CH_3$ | $NO_2$ | S | 1.5430 |
| 62 | $C_2H_5$ | $C_2H_5$ | H | Cl | $S-CH_3$ | S | 1.5568 |

TABLE 1-continued

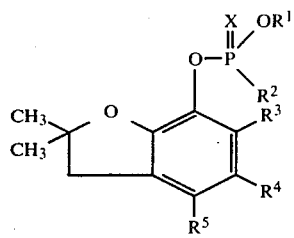

| Compound No. | $R^1$ | $R^2$ | $R^3$ | $R^4$ | $R^5$ | X | Physical Property |
|---|---|---|---|---|---|---|---|
| 63 | $C_2H_5$ | $C_2H_5$ | H | Cl | $NO_2$ | S | m.p. 59–61° C. |
| 64 | $C_2H_5$ | $C_2H_5$ | Cl | Cl | Cl | S | $N_D^{25}$ 1.5417 |
| 65 | $C_2H_5$ | $C_2H_5$ | H | H | $CF_3$ | S | 1.4936 |

Further, the present invention includes the following specific compounds.

O-Ethyl-S-n-propyl-O-(2,3-dihydro-2,2-dimethyl-6-chloro-7-benzofuranyl)thiophosphate O-Ethyl-S-n-propyl-O-(2,3-dihydro-2,2-dimethyl-6-chloro-7-benzofuranyl)dithiophosphate O-Ethyl-S-n-propyl-O-(2,3-dihydro-2,2-dimethyl-4-methylthio-7-benzofuranyl)dithiophosphate O-Ethyl-S-n-propyl-O-(2,3-dihydro-2,2-dimethyl-4-methylsulfinyl-7-benzofuranyl)thiophosphate O-Ethyl-S-n-propyl-O-(2,3-dihydro-2,2-dimethyl-4-methylsulfonyl-7-benzofuranyl)thiophosphate O-Ethyl-S-n-propyl-O-(2,3-dihydro-2,2-dimethyl-5-fluoro-7-benzofuranyl)thiophosphate O-Ethyl-S-n-propyl-O-(2,3-dihydro-2,2-dimethyl-5-fluoro-7-benzofuranyl)dithiophosphate O-Methyl-S-n-propyl-O-(2,3-dihydro-2,2-dimethyl-4-chloro-7-benzofuranyl)thiophosphate O-Methyl-S-n-butyl-O-(2,3-dihydro-2,2-dimethyl-4-chloro-7-benzofuranyl)thiophosphate O-Methyl-S-t-butyl-O-(2,3-dihydro-2,2-dimethyl-4-methylthio-7-benzofuranyl)thiophosphate O-Ethyl-S-ethyl-O-(2,3-dihydro-2,2-dimethyl-4-methylthio-7-benzofuranyl)thiophosphate O-Ethyl-S-t-butyl-O-(2,3-dihydro-2,2-dimethyl-4-trifluoromethyl-7-benzofuranyl)thiophosphate O-Ethyl-S-i-propyl-O-(2,3-dihydro-2,2-dimethyl-5-chloro-4-methylthio-7-benzofuranyl)thiophosphate O-Methyl-S-methyl-O-(2,3-dihydro-2,2-dimethyl-4-cyano-7-benzofuranyl)dithiophosphate O-Ethyl-O-(2,3-dihydro-2,2-dimethyl-4-bromo-5-chloro-7-benzofuranyl)ethylthiophosphonate O-Ethyl-O-(2,3-dihydro-2,2-dimethyl-5-bromo-4-chloro-7-benzofuranyl)ethylthiophosphonate O-Ethyl-O-(2,3-dihydro-2,2-dimethyl-5-trifluoromethyl-7-benzofuranyl)ethylthiophosphonate O-n-Propyl-O-(2,3-dihydro-2,2-dimethyl-7-benzofuranyl)methylthiophosphonate O-i-Butyl-O-(2,3-dihydro-2,2-dimethyl-4-nitro-7-benzofuranyl)ethylthiophosphonate O-Methyl-O-(2,3-dihydro-2,2-dimethyl-5-cyano-7-benzofuranyl)n-propylthiophosphonate O-i-Butyl-O-(2,3-dihydro-2,2-dimethyl-6-chloro-7-benzofuranyl)n-propylthiophosphonate O-Methyl-O-(2,3-dihydro-2,2-dimethyl-4-chloro-7-benzofuranyl)ethylthiophosphonate O-Ethyl-O-(2,3-dihydro-2,2-dimethyl-5-fluoro-7-benzofuranyl)ethylthiophosphonate O-n-Propyl-O-(2,3-dihydro-2,2-dimethyl-5-methyl-7-benzofuranyl)ethylthiophosphonate O-Ethyl-O-(2,3-dihydro-2,2-dimethyl-4-methyl-7-benzofuranyl)ethylthiophosphonate O-Ethyl-O-(2,3-dihydro-2,2-dimethyl-4,6-dichloro-7-benzofuranyl)methylthiophosphonate O-n-Propyl-O-(2,3-dihydro-2,2-dimethyl-4,6-dichloro-7-benzofuranyl)ethylthiophosphonate O-Methyl-O-(2,3-dihydro-2,2-dimethyl-5-methyl-7-benzofuranyl)methylthiophosphonate O-Ethyl-O-(2,3-dihydro-2,2-dimethyl-4-cyano-5-methyl-7-benzofuranyl)ethylthiophosphonate O-Methyl-O-(2,3-dihydro-2,2-dimethyl-5,6-dichloro-4-nitro-7-benzofuranyl)methylthiophosphonate O-Ethyl-O-(2,3-dihydro-2,2-dimethyl-5,6-dichloro-4-cyano-7-benzofuranyl)methylthiophosphonate O-n-Propyl-O-(2,3-dihydro-2,2-dimethyl-4,5,6-trifluoro-7-benzofuranyl)methylthiophosphonate O-Ethyl-O-(2,3-dihydro-2,2-dimethyl-4-methylthio-7-benzofuranyl)t-butylthiophosphonate

EXAMPLES FOR FORMULATION

In the following examples, "parts" represents "parts by weight", and the Compound Nos. correspond to the Compound Nos. in Table 1.

EXAMPLE 11 (DUST)

Two parts of Compound No. 13 and 98 parts of talc were uniformly mixed and pulverized to obtain a dust.

EXAMPLE 12 (WETTABLE POWDER)

Fifty parts of Compound No. 36, 3 parts of a surfactant and 47 parts of a mixture of talc and bentonite, were uniformly mixed and pulverized to obtain a wettable powder.

EXAMPLE 13 (EMULSION)

Thirty parts of Compound No. 11 and 3 parts of sodium alkylbenzene sulfonate were uniformly dissolved in a solvent mixture comprising 37 parts of dimethylformamide and 30 parts of xylene to obtain an emulsion.

EXAMPLE 14

Pesticidal tests against tobacco cutworm 25 mg of each compound shown in Table 1, was dissolved in 5 ml of acetone and further diluted with 45 ml of an aqueous solution containing 200 ppm of Sorpol 3005X (Trade name for a surfactant manufactured by Toho Chemical Industry Co., Ltd.) to prepare a pesticidal solution with a concentration of the compound being 500 ppm. To this 500 ppm pesticidal solution, an aqueous Sorpol 3005X solution (200 ppm) was added to prepare diluted pesticidal solutions with concentrations of 250 ppm, 100 ppm and 50 ppm.

Two cabbage leaves of 5×5 cm (25 cm$^2$) were immersed in each of the diluted pesticidal solutions having the above-mentioned concentrations for one minute and dried in air at room temperature. Separately, five larvae of tobacco cutworm in the third instar were immersed in each diluted pesticidal solution for one minute and, after removing the excess pesticidal solution attached on the bodies by means of a filter paper, fed on the treated leaves mentioned above. The larvae on the cabbage leaves were kept in an artificially illuminated chamber at 25° C. Twenty-four hours later, the survival or death of tobacco cutworm was investigated, and the mortality rate was calculated. The results thereby obtained are shown in Table 2.

EXAMPLE 15

Pesticidal tests against green peach aphid and two spotted spider mite

In the same manner as in Example 14, a pesticidal solution of each compound was prepared. Radish seedlings infested with green peach aphid and French bean seedlings infested with two-spotted spider mite were immersed in a few seconds in the pesticidal solution having a predetermined concentration, then dried in air at room temperature, and kept in an artificially illuminated chamber at 25° C. Upon expiry of 24 hours after the treatment with the pesticidal solution, the survival and death of green peach aphid and two-spotted spider mite were investigated. From the comparison with the number of infested insects or acarines preliminarily investigated prior to the treatment with the pesticidal solution, the mortality rate or acaricidal rate (%) was calculated. The results thereby obtained are shown in Table 2.

EXAMPLE 16

Pesticidal tests against brown planthopper and green rice leafhopper

In the same manner as in Example 14, a pesticidal solution of each compound was prepared. Five larvae of each of brown planthopper and green rice leafhopper in the middle instar, were released on paddy field rice seedlings set in a glass cylinder having a diameter of 3 cm and a length of 13 cm, and the upper end of the cylinder was covered with a saran net. To the test larvae and rice seedlings in the glass cylinder, 0.5 ml of a pesticidal solution having a predetermined concentration was applied by means of a small spray, and after drying it in air at room temperature, they were kept at 25° C. in an artificially illuminated chamber. Upon expiry of 24 hours after the treatment with the pesticidal solution, the survival and death of brown planthopper and green rice leafhopper were investigated, and the mortality rates were calculated. The results thereby obtained are shown in Table 2.

EXAMPLE 17

Pesticidal tests against adzuki bean weevil

In the same manner as in Example 14, a pesticidal solution of each compound was prepared. Ten adult adzuki bean weevil within 24 hours after emergence, were released in a glass tube having a diameter of 3 cm and a length of 13 cm, and the top of the tube was covered with a saran net. To the test insects in the glass tube, 0.5 ml of the pesticidal solution having a predetermined concentration, was applied by means of a small spray, and after drying it in air at room temperature, the glass tube was kept in an artificially illuminated chamber at 25° C. Upon expiry of 24 hours after the treatment with the pesticidal solution, the survival and the death of the insects were investigated, and the mortality rate was calculated. The results thereby obtained are shown in Table 2.

TABLE 2

| Compounds | | Mortality Rate (%) | | | | | |
|---|---|---|---|---|---|---|---|
| No. | Concentration (ppm) | tobacco cutworm | green peach aphid | two spotted spider mite | brown plant hopper | green rice leaf hopper | adzuki bean weevil |
| 1 | 500 | 90 | 85 | 50 | 0 | 0 | 73 |
| 2 | 500 | 90 | 63 | 38 | 0 | 0 | 81 |
| 4 | 100 | 100 | 97 | 100 | 30 | 10 | 95 |
|   | 50 | 100 | 96 | 100 | 0 | 0 | 86 |
| 5 | 100 | 100 | 45 | 83 | 30 | 20 | 91 |
|   | 50 | 60 | 16 | 83 | 20 | 0 | 50 |
| 6 | 100 | 100 | 100 | 100 | 20 | 0 | 98 |
|   | 50 | 100 | 100 | 100 | 0 | 0 | 92 |
| 7 | 100 | 100 | 100 | 100 | 20 | 0 | 99 |
|   | 50 | 100 | 92 | 75 | 0 | 0 | 63 |
| 9 | 100 | 100 | 100 | 100 | 20 | 30 | 96 |
|   | 50 | 100 | 100 | 100 | 10 | 10 | 71 |
| 10 | 100 | 100 | 79 | 100 | 20 | 30 | 100 |
|   | 50 | 50 | 73 | 100 | 0 | 0 | 100 |
| 13 | 100 | 100 | 100 | 100 | 40 | 0 | 100 |
|   | 50 | 100 | 100 | 100 | 0 | 0 | 91 |
| 14 | 100 | 100 | 100 | 100 | — | — | 100 |
| 15 | 100 | 100 | 100 | 100 | — | — | 100 |
| 16 | 100 | 100 | 100 | 100 | — | — | 100 |
| 17 | 100 | 100 | 100 | 100 | — | — | 100 |
| 19 | 500 | 100 | 100 | 100 | 40 | 20 | 100 |
|   | 250 | 95 | 100 | 93 | 30 | 20 | 100 |
| 27 | 100 | 100 | 100 | 100 | — | — | 100 |
| 29 | 100 | 100 | 100 | 100 | — | — | 100 |
| 33 | 100 | 100 | 100 | 100 | — | — | 100 |
| 36 | 100 | 100 | 100 | 100 | — | — | 100 |
| 44 | 500 | 0 | 45 | 5 | 30 | 30 | 0 |
| 45 | 500 | 20 | 100 | 75 | 40 | 10 | 30 |
| 47 | 100 | 20 | 100 | 70 | 100 | 10 | 100 |
|   | 50 | 0 | 100 | 0 | 100 | 0 | 100 |
| 49 | 100 | 0 | 100 | 100 | 80 | 0 | 45 |
|   | 50 | 0 | 89 | 100 | 50 | 0 | 20 |
| 50 | 100 | 100 | 100 | 100 | — | — | 100 |
| 52 | 100 | 100 | 100 | 65 | 100 | 10 | 100 |
|   | 50 | 90 | 100 | 23 | 100 | 0 | 100 |
| 53 | 500 | 20 | 100 | 0 | 10 | 10 | 68 |
| 54 | 500 | 0 | 100 | 0 | 90 | 60 | 100 |
| 55 | 500 | 100 | 100 | 15 | 30 | 0 | 100 |
| 58 | 500 | 20 | 100 | 9 | 45 | 0 | 95 |
| 59 | 500 | 0 | 100 | 71 | 20 | 10 | 100 |
| 63 | 250 | 75 | 100 | 75 | 100 | 30 | 75 |
|   | 100 | 10 | 100 | 25 | 85 | 0 | 50 |
| 65 | 100 | 100 | 100 | 100 | — | — | 100 |

EXAMPLE 18 (COMPARATIVE TESTS WITH KNOWN COMPOUNDS)

The pesticidal effects were compared as between the compounds of the present invention and known compounds, in the same manner as in Example 14. The results thereby obtained are shown in Table 3.

The known compounds used, were the following compounds disclosed in U.S. Pat. No. 3,839,511.

Compound A: O-ethyl-S-propyl-O-(4-chlorophenyl)-thiophosphate

Compound B: O-ethyl-S-propyl-O-(2,4-dichlorophenyl)thiophosphate

Compound C: O-ethyl-S-propyl-O-(4-methylthiophenyl)thiophosphate

EXAMPLE 19

The pesticidal effects were compared as between the compounds of the present invention and the known compounds, in the same manner as in Example 15. The known compounds used were the same as used in Example 15. The results therby obtained are shown in Table 4.

TABLE 3

| Compound No. | Tobacco cutworm Mortality Rate (%) Concentration | | |
|---|---|---|---|
| | 100 ppm | 50 ppm | 25 ppm |
| 11 | 100 | 100 | 100 |
| 13 | 100 | 100 | 100 |
| 17 | 100 | 100 | 100 |
| 19 | 100 | 100 | 98 |
| 29 | 100 | 100 | 100 |
| 33 | 100 | 100 | 100 |
| 36 | 100 | 100 | 100 |
| 41 | 100 | 100 | 100 |
| 50 | 100 | 100 | 100 |
| A | 90 | 20 | 0 |
| B | 95 | 0 | 0 |
| C | 60 | 0 | 0 |

TABLE 4

| Compound No. | Green peach aphid Mortality rate (%) | | | Two spotted spider mite Mortality rate (%) | | |
|---|---|---|---|---|---|---|
| | Concentration | | | | | |
| | 20 ppm | 10 ppm | 5 ppm | 100 ppm | 50 ppm | 25 ppm |
| 11 | 100 | 100 | 100 | 100 | 100 | 96 |
| 13 | 100 | 100 | 95 | 100 | 100 | 100 |
| 17 | 100 | 100 | 100 | 100 | 100 | 90 |
| 19 | 100 | 100 | 90 | 100 | 100 | 100 |
| 29 | 100 | 100 | 100 | 100 | 100 | 100 |
| 33 | 100 | 100 | 100 | 100 | 100 | 95 |
| 36 | 100 | 100 | 95 | 100 | 100 | 100 |
| 41 | 100 | 100 | 100 | 100 | 100 | 92 |
| 50 | 100 | 100 | 100 | 100 | 100 | 90 |
| A | 100 | 60 | 10 | 80 | 40 | 0 |
| B | 100 | 70 | 15 | 60 | 20 | 0 |
| C | 100 | 40 | 0 | 50 | 10 | 0 |

We claim:

1. An organophosphoric acid ester represented by the general formula:

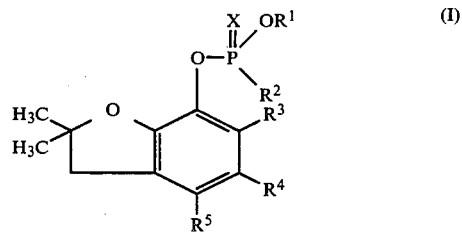

where $R^1$ is an alkyl group, $R^2$ is an alkyl group or a thioalkyl group, each of $R^3$, $R^4$ and $R^5$ is a hydrogen atom, a halogen atom, an alkylthio group, a nitro group, a cyano group, an alkyl group, an alkylsulfinyl group, an alkylsulfonyl group or a trifluoromethyl group, and X is an oxygen atom or a sulfur atom.

2. The organophosphoric acid ester according to claim 1, wherein in the general formula I, X is an oxygen atom, $R^1$ is a $C_1$–$C_4$ alkyl group, and $R^2$ is a $C_1$–$C_4$ alkylthio group.

3. The organophosphoric acid ester according to claim 2, wherein in the general formula I, X is an oxygen atom, $R^1$ is an ethyl group and $R^2$ is a propylthio group.

4. The organophosphoric acid ester according to claim 1, wherein in the general formula I, X is a sulfur atom, each of $R^1$ and $R^2$ is a $C_1$–$C_4$ alkyl group.

5. The organophosphoric acid ester according to claim 1, wherein in the general formula I, $R^1$ is a $C_1$–$C_4$ alkyl group, $R^2$ is a $C_1$–$C_4$ alkyl group or a $C_1$–$C_4$ alkylthio group provided that $R^2$ is the alkylthio group when X is an oxygen atom and $R^2$ is the alkyl group when X is a sulfur atom, and at least one of $R^3$, $R^4$ and $R^5$ is a nitro group, a cyano group, a chlorine atom, a methylthio group or a trifluoromethyl group.

6. The organophosphoric acid ester according to claim 1, wherein the compound of the formula I is selected from the group consisting of O-ethyl-S-n-propyl-O-(2,3-dihydro-2,2-dimethyl-4-chloro-7-benzofuranyl)-thiophosphate, O-ethyl-S-n-propyl-O-(2,3-dihydro-2,2-dimethyl-5-chloro-7-benzofuranyl)thiophosphate, O-ethyl-S-n-propyl-O-(2,3-dihydro-2,2-dimethyl-4,5-dichloro-7-benzofuranyl)thiophosphate, O-ethyl-S-n-propyl-O-(2,3-dihydro-2,2-dimethyl-4-methylthio-7-benzofuranyl)thiophosphate, O-ethyl-S-n-propyl-O-(2,3-dihydro-2,2-dimethyl-5-methylthio-7-benzofuranyl)thiophosphate, O-ethyl-S-n-propyl-O-(2,3-dihydro-2,2-dimethyl-4-trifluoromethyl-7-benzofuranyl)thiophosphate, O-ethyl-S-n-propyl-O-(2,3-dihydro-2,2-dimethyl-4,5,6-trichloro-7-benzofuranyl)-thiophosphate, O-ethyl-S-n-propyl-O-(2,3-dihydro-2,2-dimethyl-5-chloro-4-methylthio-7-benzofuranyl)thiophosphate, and O-ethyl-O-(2,3-dihydro-2,2-dimethyl-4-methylthio-7-benzofuranyl)ethylthionophosphate.

7. A pesticidal composition comprising an active ingredient selected from the organophosphoric acid esters represented by the general formula:

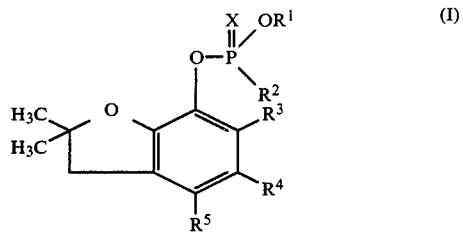

where $R^1$ is an alkyl group, $R^2$ is an alkyl group or a thioalkyl group, each of $R^3$, $R^4$ and $R^5$ is a hydrogen atom, a halogen atom, an alkylthio group, a nitro group, a cyano group, an alkyl group, an alkylsulfinyl group, an alkylsulfonyl group or a trifluoromethyl group, and X is an oxygen atom or a sulfur atom, and an adjuvant.

8. The pesticidal composition according to claim 7 comprising from 0.5 to 90% by weight of the active ingredient of the general formula I, and from 10 to 99.5% by weight of the adjuvant.

* * * * *